US011684501B2

(12) United States Patent
Poulsen et al.

(10) Patent No.: US 11,684,501 B2
(45) Date of Patent: Jun. 27, 2023

(54) MULTIPURPOSE HANDLE

(71) Applicant: Cook Medical Technologies LLC, Bloomington, IN (US)

(72) Inventors: Andreas Poulsen, Borup (DK); Mikkel Marcussen, Broenshoej (DK); Lisbeth Klarskov, Lejre (DK)

(73) Assignee: Cook Medical Technologies LLC, Bloomington, IN (US)

( * ) Notice: Subject to any disclaimer, the term of this patent is extended or adjusted under 35 U.S.C. 154(b) by 246 days.

(21) Appl. No.: 16/739,497

(22) Filed: Jan. 10, 2020

(65) Prior Publication Data

US 2020/0222218 A1 Jul. 16, 2020

Related U.S. Application Data

(60) Provisional application No. 62/791,948, filed on Jan. 14, 2019.

(51) Int. Cl.
*A61F 2/962* (2013.01)
*A61F 2/95* (2013.01)
(Continued)

(52) U.S. Cl.
CPC .......... *A61F 2/962* (2013.01); *A61B 17/1214* (2013.01); *A61F 2/01* (2013.01);
(Continued)

(58) Field of Classification Search
CPC .......... A61F 2/95; A61F 2/9517; A61F 2/954; A61F 2/958; A61F 2/962;
(Continued)

(56) References Cited

U.S. PATENT DOCUMENTS 5,066,295 A * 11/1991 Kozak .................... A61B 18/14
606/47
5,613,973 A * 3/1997 Jackson ............... A61B 17/221
606/1
(Continued)

FOREIGN PATENT DOCUMENTS

EP 1302178 A2 4/2003
WO 2012036741 A2 3/2012
(Continued)

OTHER PUBLICATIONS

European Search Report dated Apr. 24, 2020 for EP Application No. 20151467.6.

*Primary Examiner* — Kankindi Rwego
(74) *Attorney, Agent, or Firm* — Woodard, Emhardt, Henry, Reeves & Wagner, LLP

(57) ABSTRACT

A multipurpose handle incorporated into a medical device delivery system. The multipurpose handle includes an elongate handle body, an actuation button, and a locking member. The elongate handle body has a proximal end extending to a distal end, which defines a longitudinal axis. The elongate body further includes a cutout that creates a movement space therein in which the actuation button is disposed and is connected to a medical device. The actuation button is movable within the cutout along the longitudinal axis and rotatable within the cutout. The locking member is connected to the elongate handle body and movable between a locked position and unlocked position. The locking member may be in contact with the actuation button and be configured to restrict the movement of the actuation button along the longitudinal axis when in the locked position.

17 Claims, 13 Drawing Sheets

(51) Int. Cl.
*A61B 17/00* (2006.01)
*A61B 17/12* (2006.01)
*A61F 2/01* (2006.01)

(52) U.S. Cl.
CPC .............. *A61B 2017/00389* (2013.01); *A61B 2017/1205* (2013.01); *A61F 2/011* (2020.05); *A61F 2/9517* (2020.05); *A61F 2002/9528* (2013.01)

(58) Field of Classification Search
CPC ...... A61F 2002/9528; A61F 2002/9534; A61F 2/01; A61F 2/011; A61F 2/24; A61F 2/2427; A61F 2/243; A61F 2/2433; A61F 2/2436; A61F 2/2439; A61B 17/00389; A61B 17/1214; A61B 17/221; A61B 2017/1205
USPC ........................................................ 623/1.11
See application file for complete search history.

(56) References Cited

U.S. PATENT DOCUMENTS

| | | | |
|---|---|---|---|
| 5,707,376 A * | 1/1998 | Kavteladze | A61F 2/90 623/1.11 |
| 6,238,430 B1 * | 5/2001 | Klumb | A61F 2/954 623/1.13 |
| 6,258,101 B1 * | 7/2001 | Blake, III | A61B 17/221 606/113 |
| 6,572,643 B1 | 6/2003 | Gharibadeh | |
| 6,652,537 B2 | 11/2003 | Mercereau et al. | |
| 6,866,669 B2 | 3/2005 | Buzzard et al. | |
| 7,052,495 B2 | 5/2006 | Smith | |
| D598,543 S | 8/2009 | Vogel et al. | |
| 7,637,916 B2 | 12/2009 | Sandstrom | |
| 7,662,128 B2 | 2/2010 | Salcudean et al. | |
| 7,758,591 B2 | 7/2010 | Griego et al. | |
| 7,758,593 B2 | 7/2010 | Nobis et al. | |
| 7,758,625 B2 | 7/2010 | Wu et al. | |
| 7,824,443 B2 | 11/2010 | Salahieh et al. | |
| 8,021,372 B2 | 9/2011 | Blitz | |
| 8,105,337 B2 | 1/2012 | Sandstrom et al. | |
| 8,162,938 B2 | 4/2012 | Smith et al. | |
| 8,388,629 B2 | 3/2013 | Griego et al. | |
| 8,506,578 B2 | 8/2013 | Smith | |
| 8,715,302 B2 | 5/2014 | Ibrahim et al. | |
| 8,771,288 B2 | 7/2014 | Griego et al. | |
| 8,790,386 B2 | 7/2014 | Dwork | |
| 8,858,567 B2 | 10/2014 | Saleh | |
| 8,870,895 B2 | 10/2014 | Biltz | |
| 8,932,308 B2 | 1/2015 | Ibrahim et al. | |
| 8,961,534 B2 | 2/2015 | Shin | |
| 9,060,860 B2 | 6/2015 | Morris et al. | |
| 9,198,788 B2 | 12/2015 | Murray, III et al. | |
| 9,232,973 B2 | 1/2016 | Jenkins et al. | |
| 9,308,349 B2 | 4/2016 | Rezac et al. | |
| 9,468,456 B2 | 10/2016 | Raybin et al. | |
| 9,615,951 B2 | 4/2017 | Bennett et al. | |
| 9,675,369 B2 | 6/2017 | Teague et al. | |
| 9,675,485 B2 | 6/2017 | Essinger et al. | |
| 9,737,688 B2 | 8/2017 | Furnish | |
| 9,867,701 B2 | 1/2018 | Morris et al. | |
| 9,883,960 B2 | 2/2018 | Cummins et al. | |
| 9,936,965 B2 | 4/2018 | Goode et al. | |
| 10,143,475 B2 | 12/2018 | Ibramhim et al. | |
| 10,251,632 B2 | 4/2019 | Herz et al. | |
| 10,349,970 B2 | 7/2019 | Raybin et al. | |
| 10,758,351 B2 | 9/2020 | Morris et al. | |
| 10,806,897 B2 | 10/2020 | Furnish | |
| 10,874,839 B2 | 12/2020 | Hatlack et al. | |
| 10,888,349 B2 | 1/2021 | Pereira et al. | |
| 10,932,951 B2 | 3/2021 | Schaller et al. | |
| 10,939,930 B2 | 3/2021 | Teague et al. | |
| 10,973,634 B2 | 4/2021 | Cohen et al. | |
| 11,027,105 B2 | 6/2021 | Hatlock et al. | |
| 2005/0273151 A1 | 12/2005 | Fulkerson et al. | |
| 2007/0255289 A1 | 11/2007 | Nakao | |
| 2008/0249552 A1 | 10/2008 | Eliachar et al. | |
| 2009/0024084 A1 | 1/2009 | Khosla et al. | |
| 2009/0210046 A1 | 8/2009 | Shumer et al. | |
| 2011/0071490 A1 | 3/2011 | Kassab et al. | |
| 2011/0257719 A1 | 10/2011 | Argentine | |
| 2012/0053595 A1 | 3/2012 | Nakao | |
| 2012/0123528 A1 * | 5/2012 | Knippel | A61F 2/2436 623/2.11 |
| 2014/0336676 A1 | 11/2014 | Pong et al. | |
| 2015/0182225 A1 | 7/2015 | Morejohn et al. | |
| 2015/0290040 A1 | 10/2015 | Vaughan et al. | |
| 2015/0305902 A1 | 10/2015 | Argentine | |
| 2015/0335452 A1 * | 11/2015 | Rao | A61F 2/966 623/23.66 |
| 2016/0121086 A1 | 5/2016 | Castro et al. | |
| 2016/0135972 A1 | 5/2016 | Vad et al. | |
| 2016/0206456 A1 | 7/2016 | Walsh | |
| 2017/0065415 A1 | 3/2017 | Rupp et al. | |
| 2017/0080185 A1 | 3/2017 | Kassab et al. | |
| 2017/0216063 A1 | 8/2017 | Bessho | |
| 2017/0224486 A1 | 8/2017 | Delaloye et al. | |
| 2017/0238952 A1 | 8/2017 | Teague et al. | |
| 2017/0291008 A1 | 10/2017 | Hillukka et al. | |
| 2018/0132923 A1 | 5/2018 | Simani et al. | |
| 2018/0168679 A1 | 6/2018 | Oh et al. | |
| 2019/0117229 A1 | 4/2019 | Ibrahim et al. | |
| 2019/0282261 A1 | 9/2019 | Raybin et al. | |
| 2019/0388144 A1 | 12/2019 | Zhang et al. | |
| 2020/0023163 A1 | 1/2020 | Chu et al. | |
| 2020/0061340 A1 | 2/2020 | Mixter et al. | |
| 2020/0359878 A1 | 11/2020 | Schwarz | |
| 2020/0360664 A1 | 11/2020 | Regnier et al. | |
| 2021/0154450 A1 | 5/2021 | Matlock et al. | |
| 2021/0161712 A1 | 6/2021 | Schaller et al. | |

FOREIGN PATENT DOCUMENTS

| | | |
|---|---|---|
| WO | WO 2020802988 | 1/2020 |
| WO | WO 2020041716 | 2/2020 |
| WO | WO 2020230131 | 11/2020 |

* cited by examiner

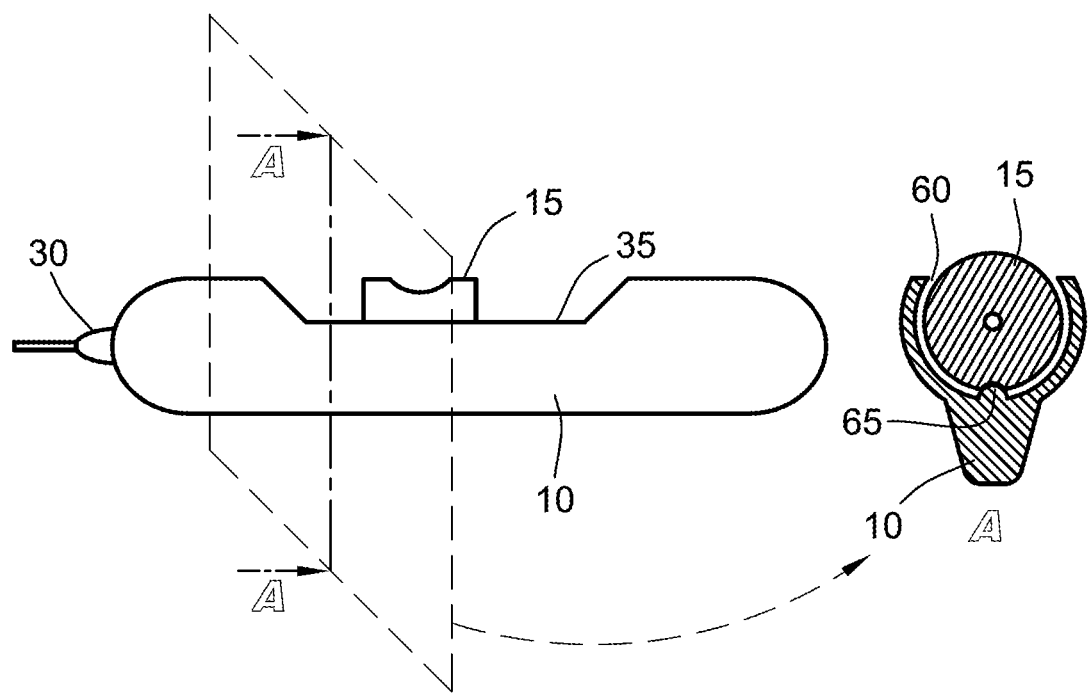
FIG. 7
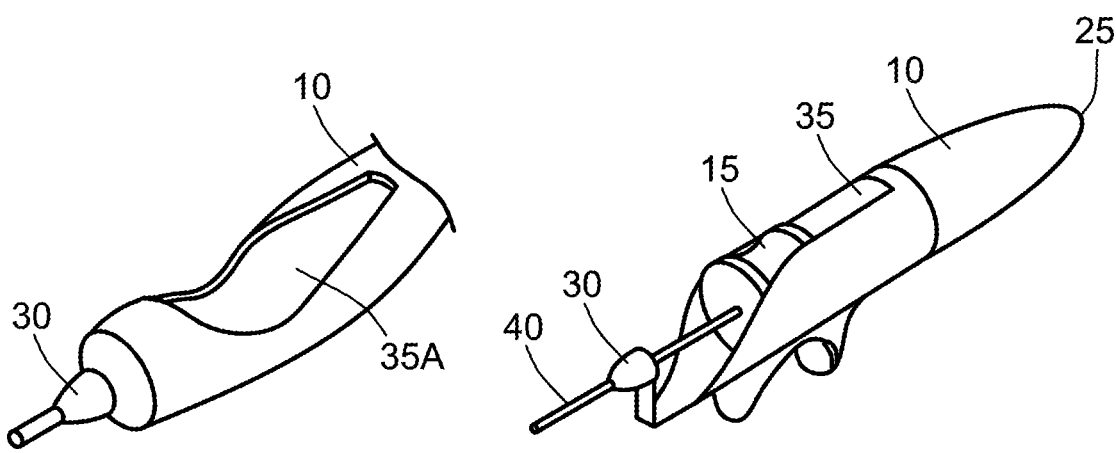
FIG. 8A  FIG. 8B

MULTIPURPOSE HANDLE

CROSS-REFERENCE TO RELATED APPLICATIONS

This application claims the benefit of the filing date under 35 U.S.C. § 119(e) of U.S. Provisional Application No. 62/791,948 filed Jan. 14, 2019, the entire contents of which is hereby incorporated herein by reference.

FIELD

The disclosure relates generally to a medical device delivery system. More specifically, this disclosure relates to a multipurpose handle for use in a medical device delivery system that is configured to control relative movements associated therewith, as well as a method of using the handle.

BACKGROUND

The statements in this section merely provide background information related to the present disclosure and may not constitute prior art.

In many medical procedures, an implant is inserted into a patient's body for treatment. For example, a vena cava filter may be deployed within a patient's vasculature in order to prevent a pulmonary embolism. In order to successfully deploy and retrieve the implant, the user (e.g., physician) needs to be able to control relative motion of various structures of a delivery and retrieval system. Many known systems require two-handed operation. However, such operation can be difficult for the user to move multiple structures in different directions while performing other functions, such as monitoring conditions at the surgery site in order to ensure patient safety.

Conventional medical device delivery systems generally operate by moving the medical device within a catheter positioned in the body of a patient along a desired vascular path or other body passageway, until the medical device reaches a desired treatment site. The deployment operation requires some measure of skill by the user because he/she must monitor the relative position of the medical device and other components within the delivery system, as well as utilize both of his/her hands to operate the delivery system. More specifically, in many conventional systems the user must hold a proximal hub attached to an inner shaft member of the delivery system in a fixed position with one hand, while simultaneously withdrawing the proximal hub attached to the outer tubular sheath with the other hand.

Accurate deployment and positioning of the device is important to ensuring patient safety. Thus, a system that provides accurate control of the movements of the medical device can improve the safety associated therewith. At the same time, it is also desirable to provide an integrated and ergonomic handle for easy and effective operation of the system. A handle that is capable of single-hand operation with a locking mechanism may provide such benefits. Accordingly, improvements can be made to a delivery and retrieval system with a handle configured for multipurpose operation.

SUMMARY

The present disclosure generally provides a medical device delivery system. More specifically, the present disclosure provides a multipurpose handle for use in a medical device delivery system that is configured to control relative movements associated therewith.

The multipurpose handle generally includes an elongate handle body, an actuation button, and a locking member. The elongate handle body has a proximal end extending to a distal end, which defines a longitudinal axis. The elongate body further includes a cutout that defines a movement space therein in which the actuation button is disposed and connected to a medical device. The actuation button is movable within the cutout along the longitudinal axis and rotatable within the cutout. The locking member is connected to the elongate handle body and movable between a locked position and unlocked position. The locking member is in contact with the actuation button in a configuration that restricts the movement of the actuation button along the longitudinal axis when in the locked position.

According to another aspect of the present disclosure, a medical device delivery system is provided. This medical device delivery system comprises an outer sheath; a medical device located at least partially within the outer sheath in an initial configuration ready for deployment; and a multipurpose handle as described above and further defined herein. The multipurpose handle connected to the outer sheath and the medical device.

According to yet another aspect of the present disclosure, the use of a medical device delivery system is described that incorporates a multipurpose handle to deliver or retrieve a medical device from a desired or targeted site within a vasculature of a patient's body. During such use, the multipurpose handle provides the user with control over longitudinal movement together with scrolling rotation of the attached medical device. The user may utilize his/her thumb and index finger on a single hand to accomplish such longitudinal and rotational movements.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings. The components in each of the drawings may not necessarily be drawn to scale, rather emphasis is placed upon illustrating the principles of the invention. Moreover, like referenced numerals in different drawings designate corresponding or similar components or elements.

FIG. 7 is a perspective view and a cross-sectional view of an elongated handle body that may be used in the multipurpose handle.

FIG. 8A and FIG. 8B are perspective views of cutouts made in the elongated handle body according to the teachings of the present disclosure.

Figure 1:
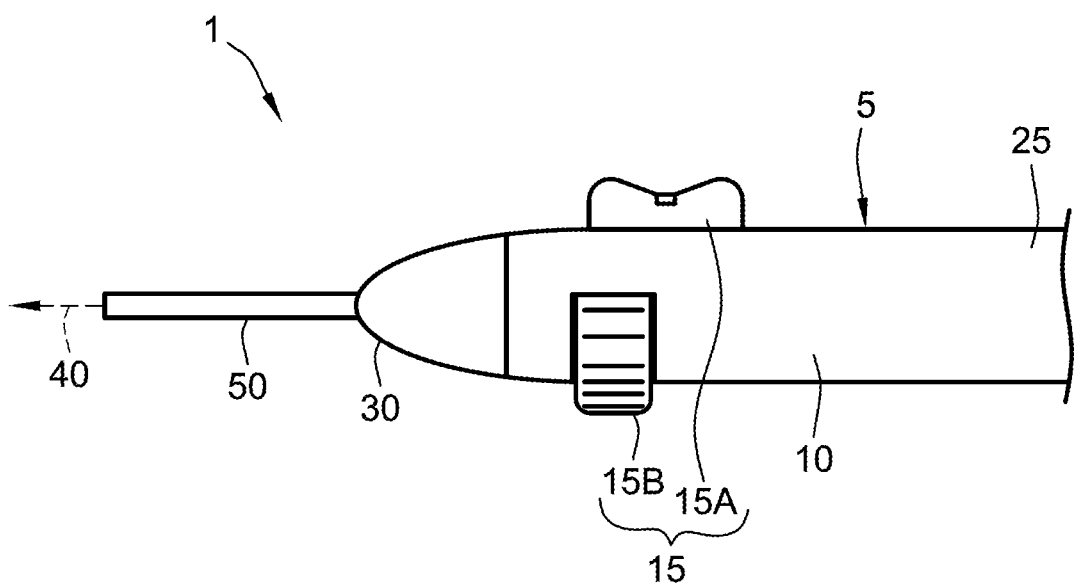
FIG. 1 is a perspective view of a medical device delivery system having a multipurpose handle formed according to the teachings of the present disclosure.

The drawings described herein are for illustration purposes only and are not intended to limit the scope of the present disclosure in any way.

DETAILED DESCRIPTION

The following description is merely exemplary in nature and is in no way intended to limit the present disclosure or its application or uses. For example, the multipurpose handle made and used according to the teachings contained herein is described throughout the present disclosure in conjunction with deploying or retrieving a vena cava filter treating a pulmonary embolism in order to more fully illustrate the structural elements and the use thereof. The incorporation and use of such a multipurpose handle in other applications, including without limitation the deployment of a stent, is contemplated to be within the scope of the present disclosure. The multipurpose handle may be incorporated in any delivery system that includes an outer sheath that surrounds an inner shaft configured to carry a medical device therein for delivery to a desired target-site in a vasculature within the body. The multipurpose handle may be incorporated into a device of any type or size provided the mandrill size necessary to form the handle does not exceed the dimensions associated with manufacturing the handle to fit inside a human hand. It should be understood that throughout the description, corresponding reference numerals indicate like or corresponding parts and features.

The present disclosure generally provides a medical device delivery system. More specifically, the present disclosure provides a multipurpose handle for use in a medical device delivery system configured to control relative movements associated therewith. As such, the medical device delivery system of the present disclosure is provided with an integrated and ergonomic handle that replaces the functions of separate proximal hubs in conventional systems, while providing a desirable dual mode of operation with a locking function.

The handle design generally comprises a hollow tube with an inner moving part, capable of both sliding and rotating along with a locking member or mechanism that secures the inner part from longitudinal movement in the back-most position. The locking mechanism may have an audible and/or sensible confirmation of lock. The locking member or mechanism is configured to resist inadvertent or accidental movement or retraction of the various components within the medical device delivery system during packaging, sterilization, shipping, storage, handling, and preparation for use. The lock may be spring-loaded, or otherwise easily released as further described herein.

The use of this multipurpose handle allows the user to have control over longitudinal movement together with scrolling rotation of the attached medical device. The medical device delivery system may be utilized in any procedure or other operation where a medical device is required to slide forwards/backwards and/or rotate in order to be successfully deployed. According to another aspect of the present disclosure, the multipurpose handle involves the use of a single actuator for multiple modes of operating the handle and delivery system.

A medical device delivery system that incorporates the multipurpose handle of the present disclosure is capable of providing a variety of benefits and advantages. These benefits include, without limitation, one or more of the following:

(i) single-handed operation of the medical device delivery system;

(ii) a mechanism that provides leverage or mechanical advantage in adjusting or reducing the forces needed to operate the system;

(iii) improved accuracy in positioning the medical device at the target-site;

(iv) multiple modes of operation;

(v) an integrated and ergonomic handle for operating the system;

(vi) a locking mechanism capable of resisting inadvertent or accidental movement or retraction of the delivery system; and (vii) the ability to hold the delivery system components in a fixed relative position during an intermediate stage in the deployment of the medical device.

For the purpose of this disclosure, the term "proximal" refers to a direction that is generally towards an user (e.g., physician) during a medical procedure, while the term "distal" refers to a direction that is generally towards a target site within a patient's anatomy during the medical procedure.

For the purpose of this disclosure, the terms "about" and "substantially" are used herein with respect to measurable values and ranges due to expected variations known to those skilled in the art (e.g., limitations and variability in measurements).

For the purpose of this disclosure, the terms "at least one" and "one or more of" an element are used interchangeably and may have the same meaning. These terms, which refer to the inclusion of a single element or a plurality of the elements, may also be represented by the suffix "(s)" at the end of the element. For example, "at least one metal", "one or more metals", and "metal(s)" may be used interchangeably and are intended to have the same meaning.

The focus of the design of the multipurpose handle and the medical device delivery system is to enhance patient safety. In this respect, the multipurpose handle makes use of an ergonomic design and one-handed operation, which places more control on the user (e.g., physician) where conventional products rely on two hands to operate the device. The safety feature is also rooted in a thumb button for both longitudinal and scrolling movement, as well as adding precision to the user, which is not found in conventional products. The multipurpose handle also includes a locking mechanism triggered by the index finger, which ensures the device may be secured without compromising the control. Overall, the user can perform all of the relevant steps required in a medical procedure, while only moving the thumb and index fingers while simultaneously maintaining a firm grip on the delivery system. In comparison to conventional delivery systems, the medical device delivery system of the present disclosure may be manipulated by a user to easily perform all necessary steps with one hand, without having to look away from the typically used radio-imaging screen.

Referring to FIGS. 1-15, the medical device delivery system 1 includes a multipurpose handle 5 that comprises an elongate handle body 10, an actuation button 15, and a locking member 20. The elongate handle body 10 has a proximal end 25 extending to a distal end 30, which defines a longitudinal axis (A). The elongate body 10 further includes a cutout 35 that creates a movement space therein. The actuation button 15 is disposed within the cutout 35 and connected to a medical device 40. The actuation button 15 may be movable within the cutout 35 along the longitudinal axis (A) and rotatable within the cutout 35. The locking member 20 is connected to the elongate handle body 10 and movable between a locked position and unlocked position. The locking member 20 may be in contact with the actuation button 15 and be configured to restrict the movement of the actuation button 15 along the longitudinal axis (A) when in the locked position.

Figure 2:
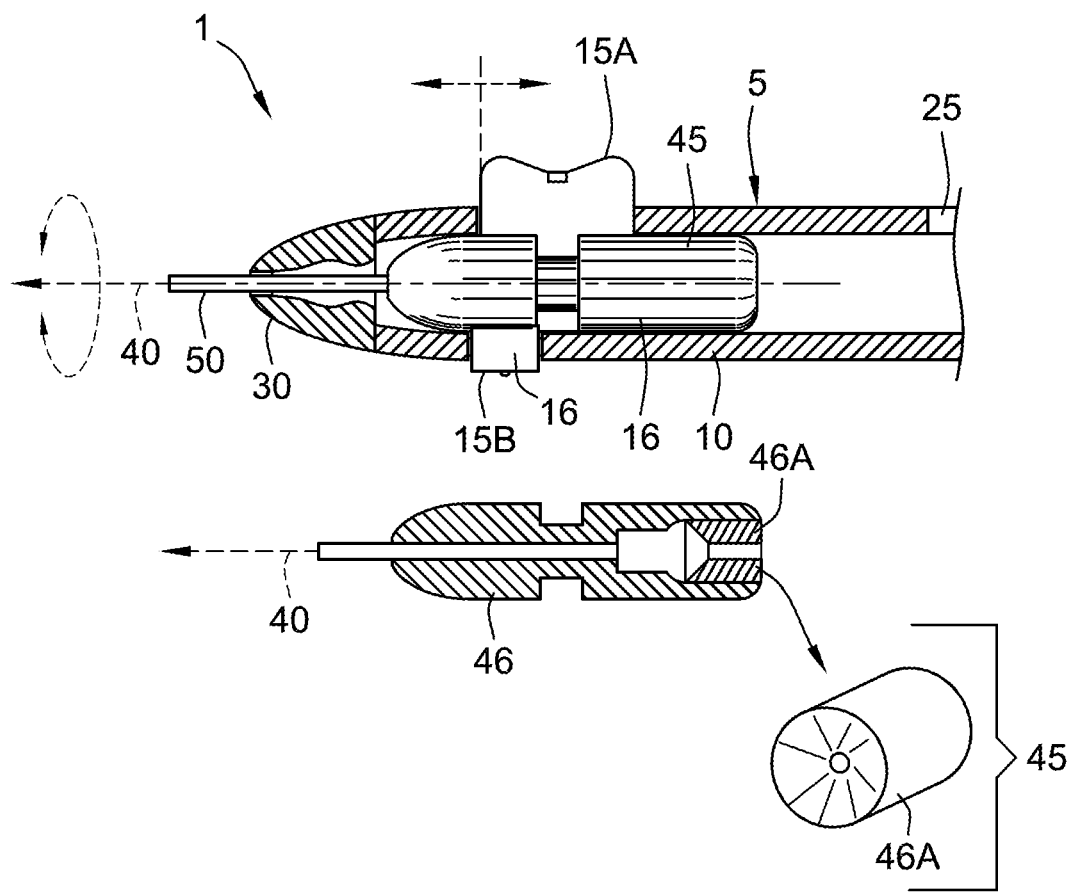
FIG. 2 is a cross-sectional view of the multipurpose handle shown in the delivery system of FIG. 1.

As shown in FIGS. 1 and 2, the actuation button 15 may include a sliding portion 15A to control the longitudinal movement of the medical device 40 and a rotating portion 15B to control rotational movement associated with the medical device 40. The sliding portion 15A and rotating portion 15B may be manipulated by different fingers of the user's hand. For example, the sliding portion 15A may be manipulated using the thumb finger, while the index finger of the user manipulates the rotating portion 15B.

Referring now to FIG. 2, one or more of the sliding portion 15A and the rotating portion 15B of the actuation button 15 may include one or more slits 16 in order to provide for added sliding and/or scrolling control. The actuation button 15 may in communication or contact with a sliding component 45 configured to secure the medical device 40. For example, this sliding component 45 may be, without limitation, a collet 46 that uses a fastener 46A or other type of anchor to secure the medical device 40.

Figure 3:
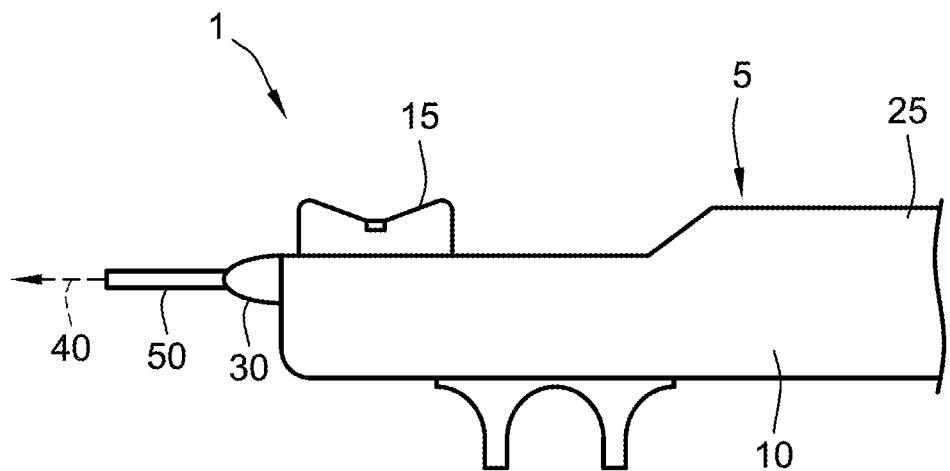
FIG. 3 is a perspective view of another medical delivery system incorporating a multipurpose handle formed according to the teachings of the present disclosure.
Figure 4:
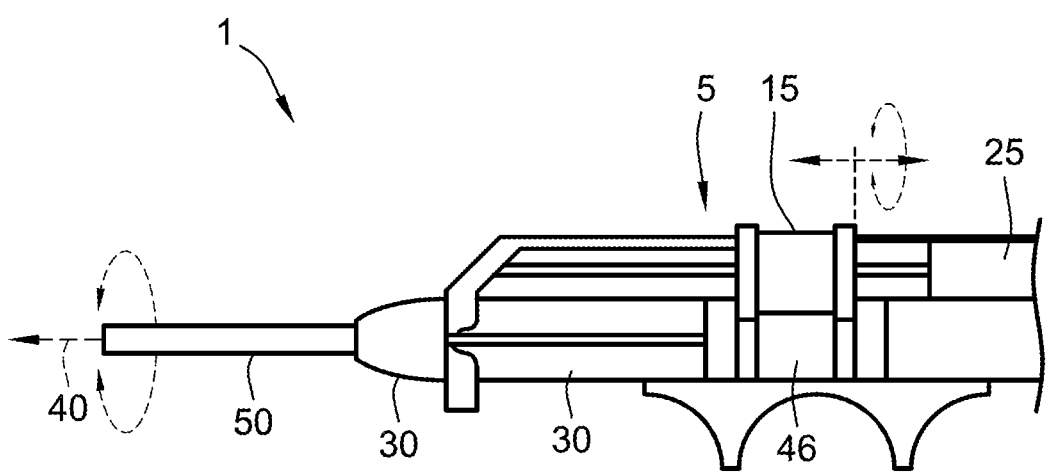
FIG. 4 is a cross-sectional view of the multipurpose handle of FIG. 3 highlighting the ability for longitudinal and rotational motion.
Figure 5:
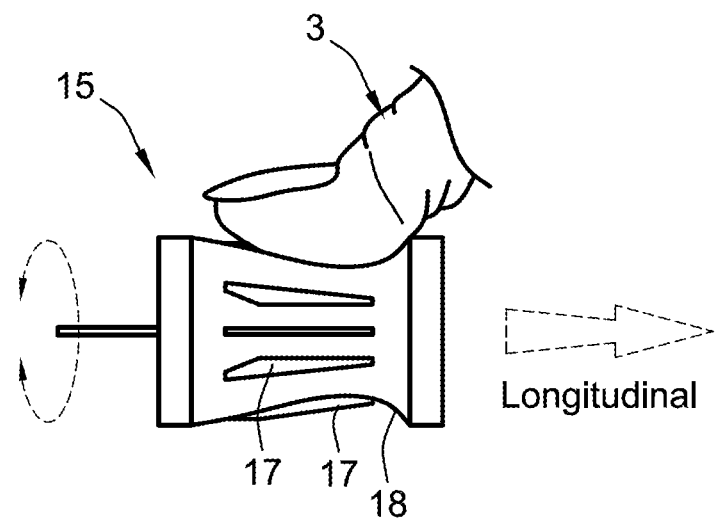
FIG. 5 is a perspective view of an actuation button that may be used in the multipurpose handle.

According to another aspect of the present disclosure as shown in FIGS. 3 and 4, the longitudinal movement and rotational movement associated with the actuation button 15 may be incorporated such that one finger of the user is capable of controlling both the longitudinal and rotational movement of the medical device by a sliding motion or a scrolling motion, respectively. For example, the actuation button 15 may be a thumb wheel capable of being manipulated solely by the thumb finger of the user (e.g., physician) in order to move the medical device 40 both longitudinally and rotationally through a sheath 50. When desirable, the actuation button 15 as shown in FIG. 5 may include one or more fins 17 and/or an indented edge 18 configured to fit a thumb finger 3 to provide for additional gripping during rotational and longitudinal movements. When the actuation button 15 is a thumb wheel the fins 17 may be disposed around the circumference of the wheel.

Figure 6:
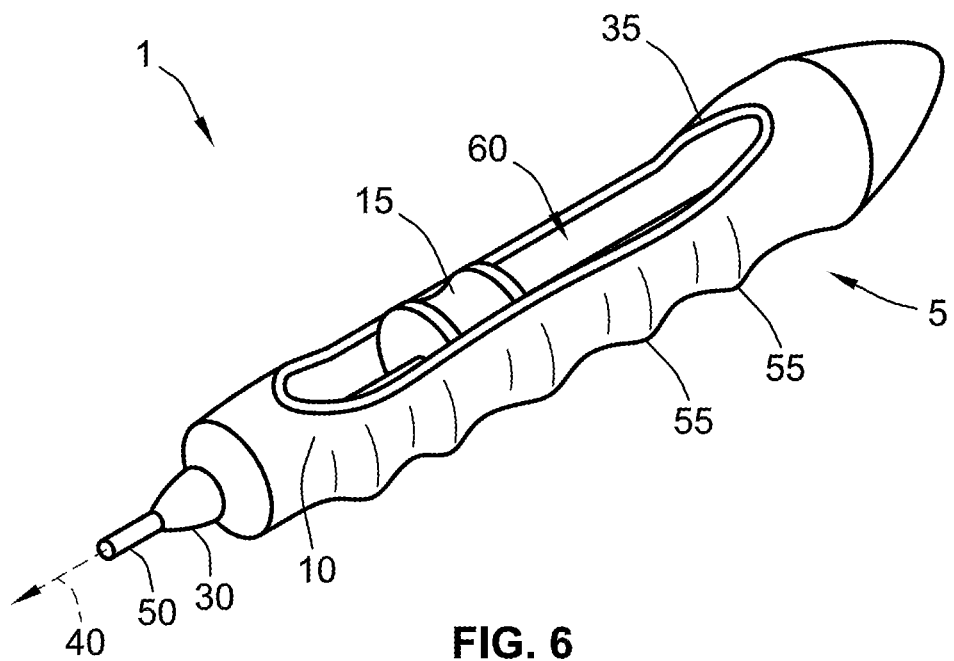
FIG. 6 is a perspective view of an elongated handle body that may be used in the multipurpose handle.

Referring now to FIG. 6, the elongate handle body 10 may include one or more gripping knurls 55, alternatively, a plurality of gripping knurls 55 for providing an user with a firm gripping surface. The elongate handle body 10 may represent a singular unified component or include a plurality of components, such as an upper body portion and a lower body portion, that are attached together by gluing, welding, melt bonding, or the like. The dimensions of the elongate handle body 10 may be customized in order to fit a specific predetermined hand size or be optimized such that various hand sizes are capable of obtaining a firm grip when using the multipurpose handle 1. Additional ergonomic features may be included in the elongate handle body as well without exceeding the scope of the present disclosure.

The multipurpose handle 5 including the elongate handle body 10, as well as the various parts contained therein may be formed from polymeric or plastic materials, ceramic materials, metals or metal alloys, and/or combinations thereof. The materials for use in the multipurpose handle 5 are selected so that they exhibit desirable or required performance characteristics, such as biocompatibility, flexibility, and strength to name a few. The polymeric or plastic materials may include one or more thermoplastic materials or thermoset materials, individually or in combination. Several examples of suitable polymeric or plastic materials may include but not limited to polyamides (e.g., nylons), polyimides, polyethylenes, polyurethanes, polyethers, polyesters, acrylonitrile butadiene styrene (ABS), and mixtures or copolymers thereof. Alternatively, the elongate handle body 10 is formed from ABS. Any metal parts used within the multipurpose handle 5 may be formed from, without limitation, stainless steel, brass, Nitinol, or a combination thereof. Alternatively, the metal parts are formed from brass.

Referring now to FIGS. 6, 7, and 8(A-B), the elongate handle body 10 may also include a cutout 35 in the form of a longitudinal slot that defines a channel 65 configured to accommodate the sliding action of the actuation button 15. This cutout or longitudinal slot 35 is capable of limiting the extent of longitudinal movement within the multipurpose handle 5. The actuation button 15 or thumb wheel that fits within the cavity 60 of the cutout 35 may include a tactile bump 65, which can be seen in the cross-section of the actuation button 15 shown in the plane (A) view of FIG. 7. This tactile bump 65 may assist the user in determining the orientation of the attached medical device 40. When desirable this longitudinal slot may be in the shape of a droplet 35A as shown in FIG. 8A. The droplet shaped cutout 35A may vary in size provided the actuation button 15 is secured and cannot slip out of the cavity 60 formed by the cutout 35A (FIG. 8B).

Figure 9A:
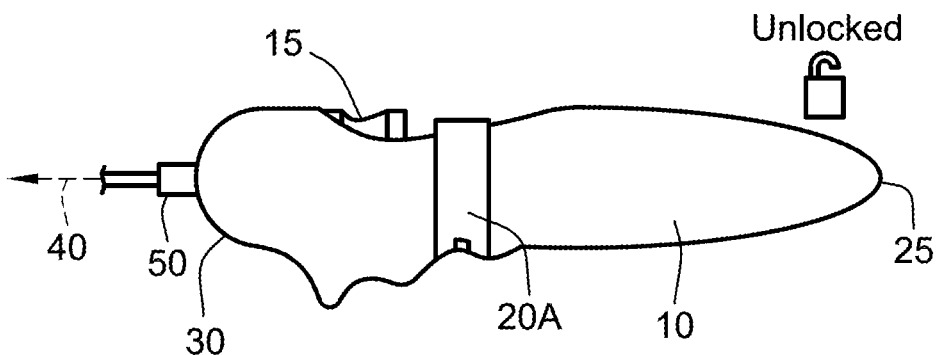
FIG. 9A and FIG. 9B are perspective views of a multipurpose handle highlighting the use of a lock ring.
Figure 9B:
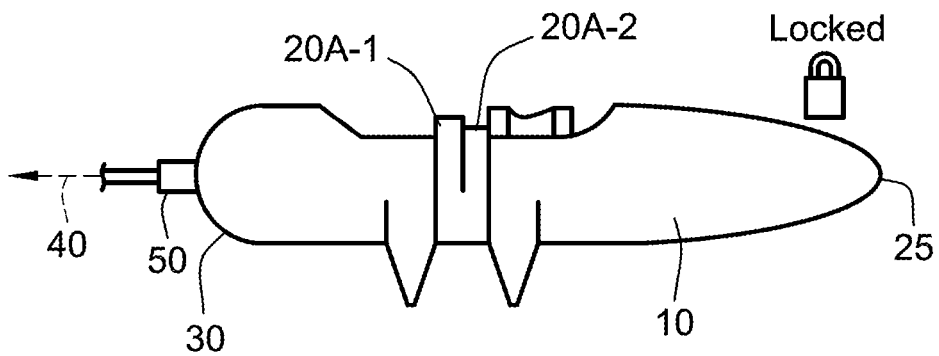
Figure 9C:
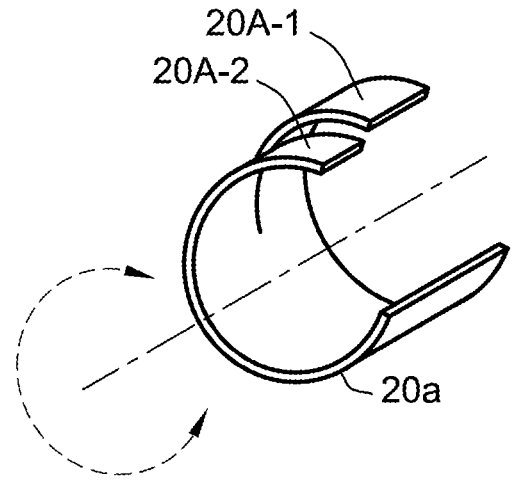
FIG. 9C is perspective view of the lock ring used in FIG. 9B.

Referring now to FIGS. 9(A-C), the locking mechanism 20 may include a locking ring 20A configured to be either be in an unlocked position or a locked position. When the locking ring 20A is unlocked, the actuation button 15 may be moved (FIG. 9A). However, when the locking ring 20A is in the locked position, the actuation button 15 is prevented from moving (FIG. 9B). The locking ring 20A may include at least one slit 67 that allows one portion of the locking ring 20A-1 to abut against the actuation button 15 when the locking ring 20A is rotated into the locked position (FIG. 9C). Another portion of the locking ring 20A-2 is located such that it grips or holds a portion of the elongated handle body 10 (FIG. 9B). Such a locking mechanism 20 may resist inadvertent or accidental movement or retraction of the actuation button 15 or other components in the multipurpose handle 5 during packaging, sterilization, shipping, storage, handling, and preparation for use.

Figure 10:
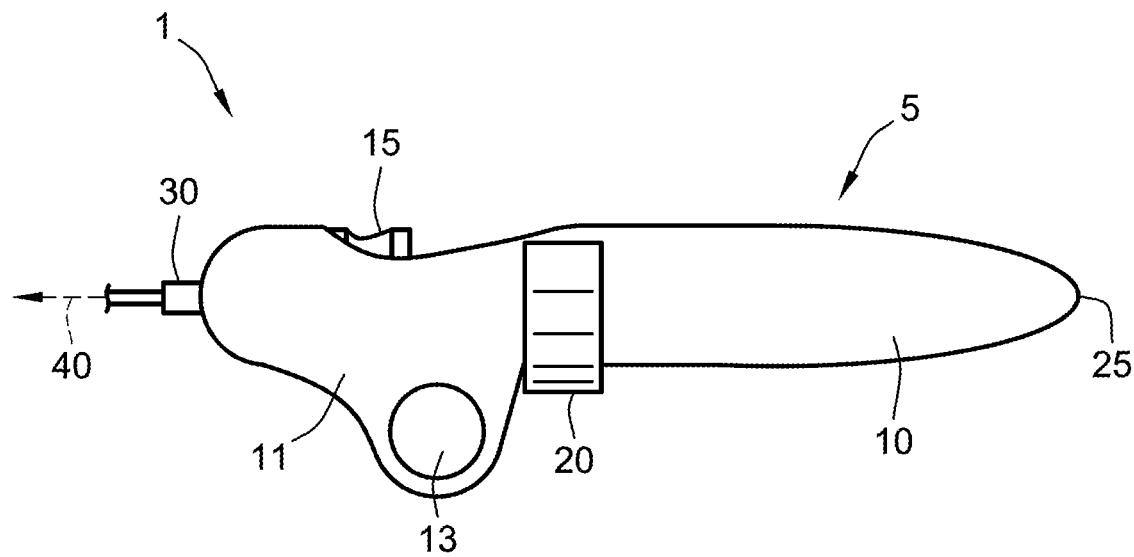
FIG. 10 is a perspective view of a multipurpose handle with a locking member formed according to the teachings of the present disclosure.
Figure 11:
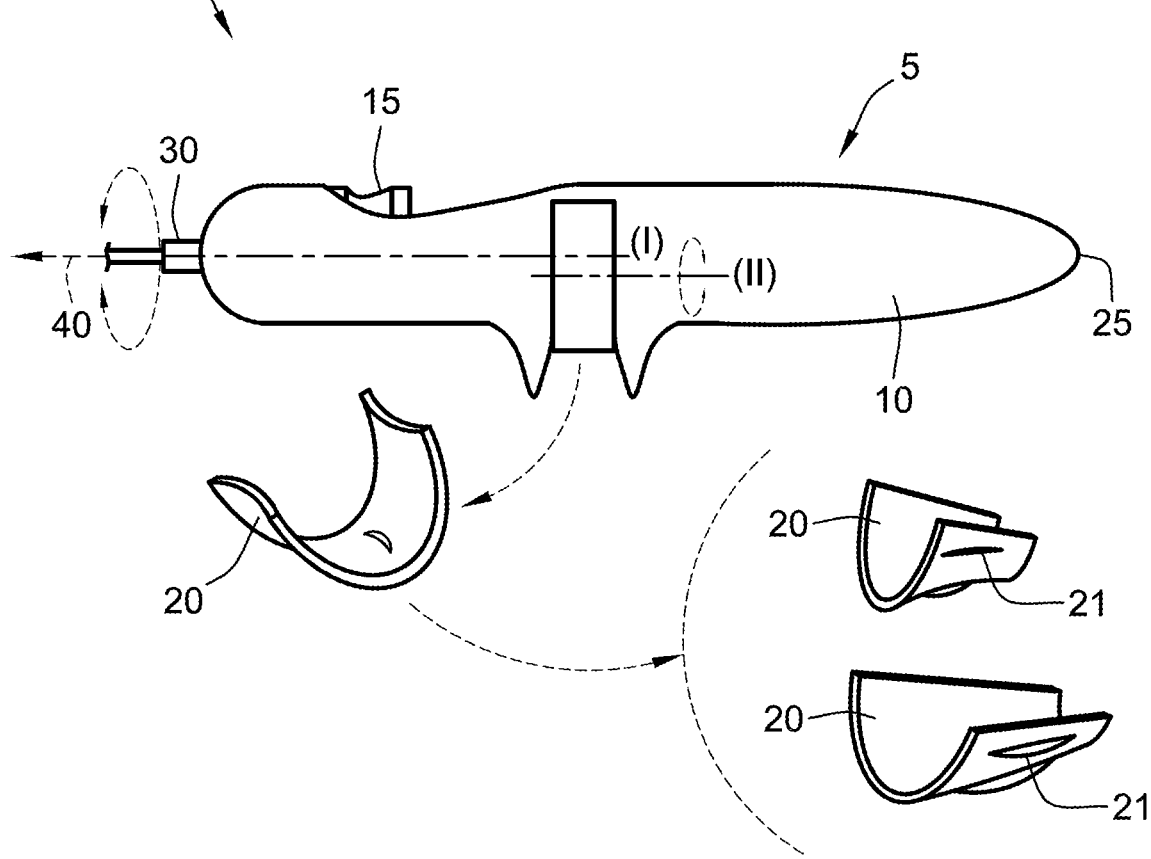
FIG. 11 is a perspective view of another multipurpose handle with a locking member formed according to the teachings of the present disclosure.

Referring now to FIGS. 10 and 11, the elongated handle body 10 may comprise a fin 11 aligned with the longitudinal axis (I) of the elongated handle body 10. This fin 11 further comprise a hole 13 located in a position that is easily accessible by the index finger of the user during the operation of the medical device delivery system 1 (see FIG. 10). The difference (A) between the longitudinal axis (I) of the elongated handle body 10 and the longitudinal axis (II) of the locking member 20 causes the locking member 30 to rotate into the elongated handle body 10 of the multipurpose handle 5 (see FIG. 11). The locking member 20 may include one or more fins 21 to assist in gripping the mechanism in order to scroll or rotate the member between locked and unlocked positions.

Figure 12A:
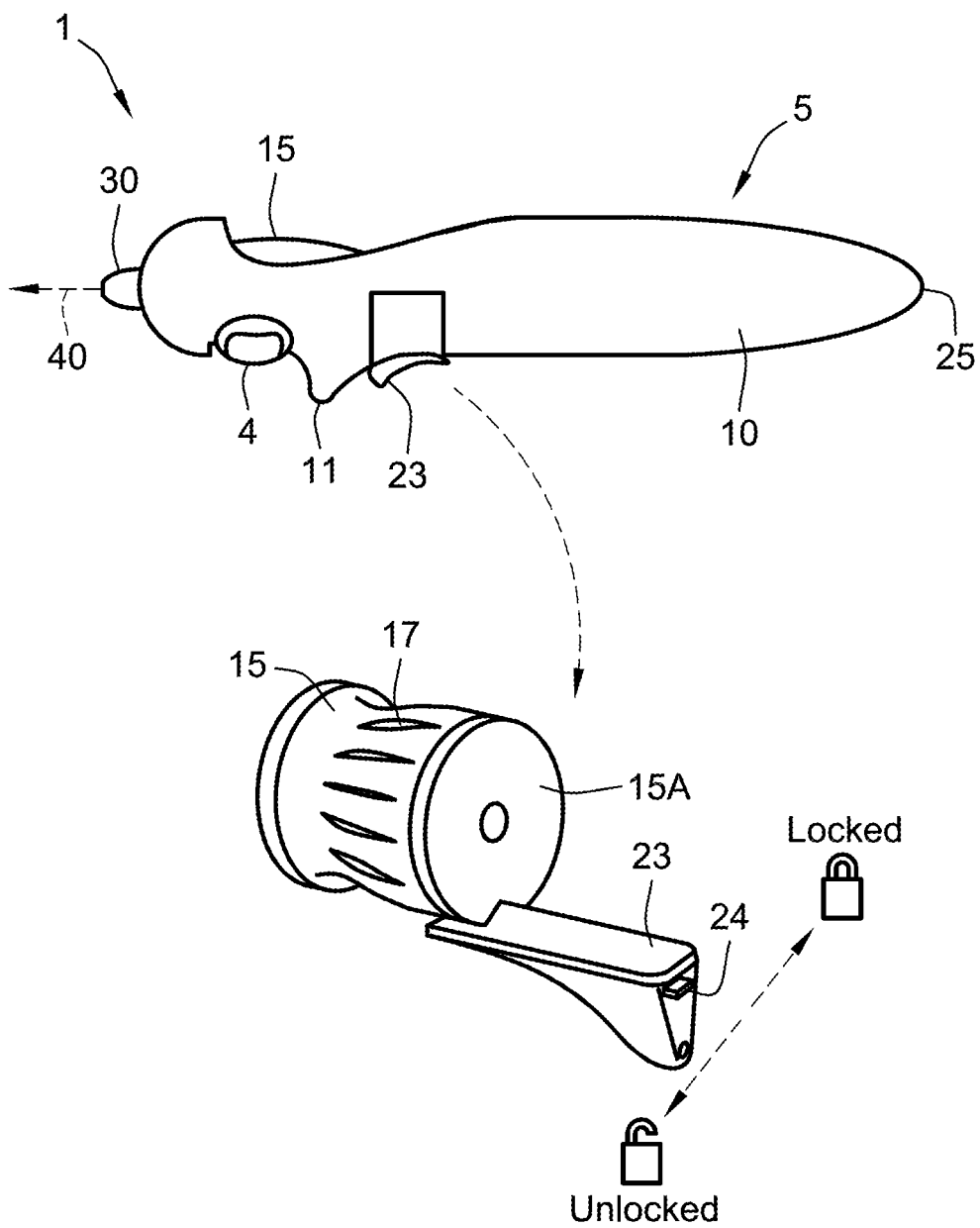
FIG. 12A is a perspective view of multipurpose handle and an expanded view of a sliding locking button.

Referring now to FIGS. 12(A)-12(E), various other forms of the locking mechanism are described. In FIG. 12A, a sliding locking button 23 is utilized. This locking button 23 slides against a portion of the actuation button 15 in order to prevent movement thereof when in the locked position. Alternatively, the locking button 23 abuts against a side and/or a face 15A of the actuation button 15 or thumb wheel. Alternatively, the locking member 20 or button 23 makes contact with the distal face 15A of the actuation button 15 or thumb wheel. The locking button 23 may slide in an opposite direction in order to unlock and allow the actuation button 15 to move. In this embodiment, the index finger 4 of the user may, together with the thumb finger provide greater control of the actuation button 15.

Figure 12B:
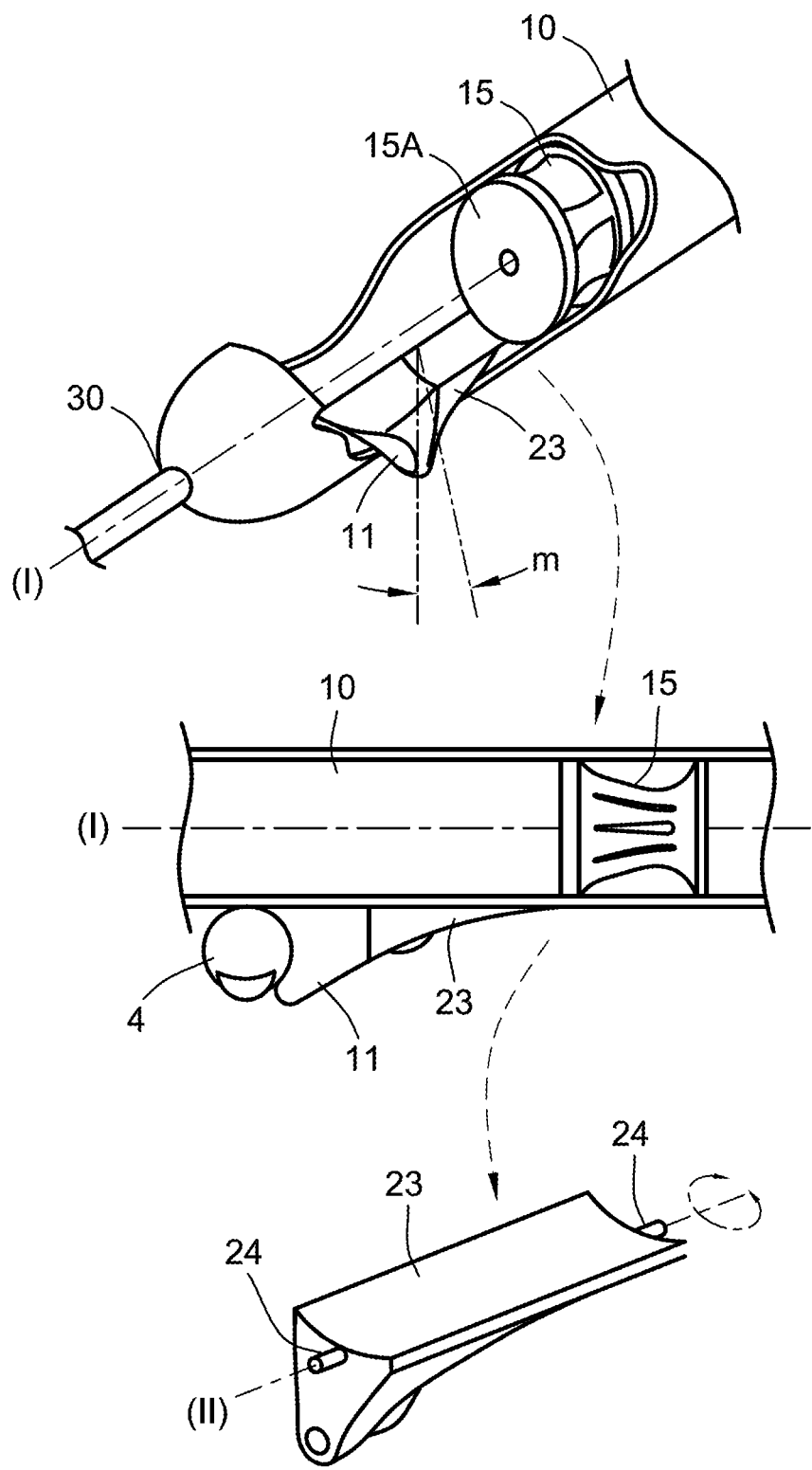
FIG. 12B is perspective view and a cross-sectional view of a multipurpose handle incorporating another locking button according to the teachings of the present disclosure.

In FIG. 12B, the locking button 23 is shown to abut against a face 15A of the actuation button 15. In this embodiment the fin 11 in contact with the user's middle or index finger 4 is capable of movement (m) causing the locking button 23 to engage the face 15A of the actuation button 15 in order to establish a locked position. The locking button 23 may be held in place through the use of one or more fasteners 24 formed as part of the locking button 23.

Figure 12C:
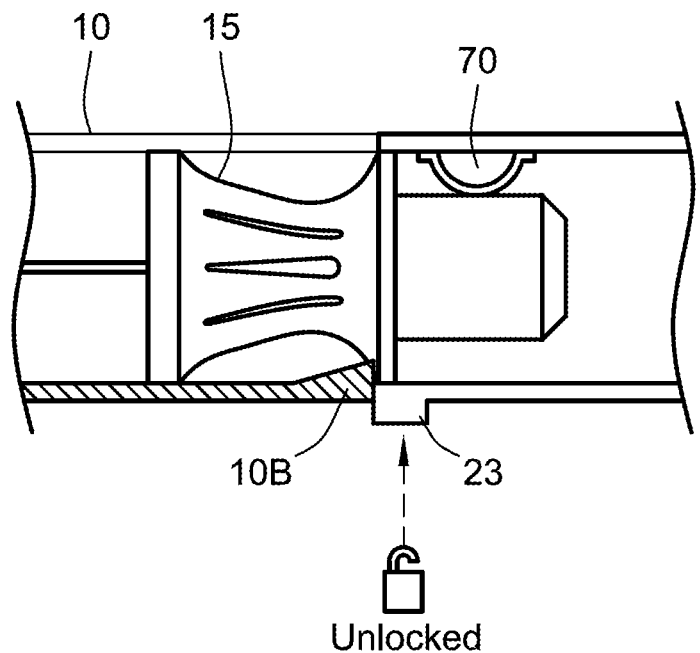
FIG. 12C is a cross-sectional view of a multipurpose handle incorporating another locking button according to the teachings of the present disclosure.

In another configuration shown in FIG. 12C, the actuation button 15 may slide over a projection 10B arising from a wall of the elongate handle body 10 to create a locked position. In this locked position, the actuation button 15 is held in place by a spring 70. The actuation button 15 may be released, thereby, creating an unlocked position through the use of the locking button 23. The locking button 23 in this case is a push button that overcomes the spring 70 retention and moves the actuation button 15 past the projection 10B in the wall of the elongate body handle 10.

Figure 12D:
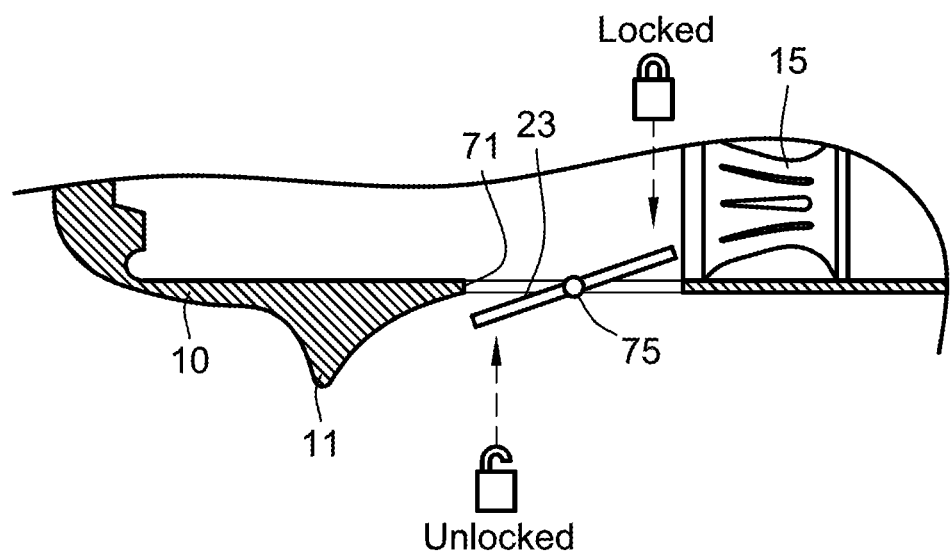
FIG. 12D is a cross-sectional view of another multipurpose handle incorporating a different locking button according to the teachings of the present disclosure.

Another form of the locking member 20 is shown in FIG. 12D in which the locking button 23 is a spring-loaded lever capable of being pivoted near its fulcrum point 75. A spring 71 is positioned such that the locking button 23 is held in a locked position by the spring 71 forcing the lever to contact a face 15A of the actuation button 15. The user is able to release the actuation button 15 by pushing on the locking button 23, thereby overcoming the spring 71 retention and creating an unlocked position.

Figure 12E:
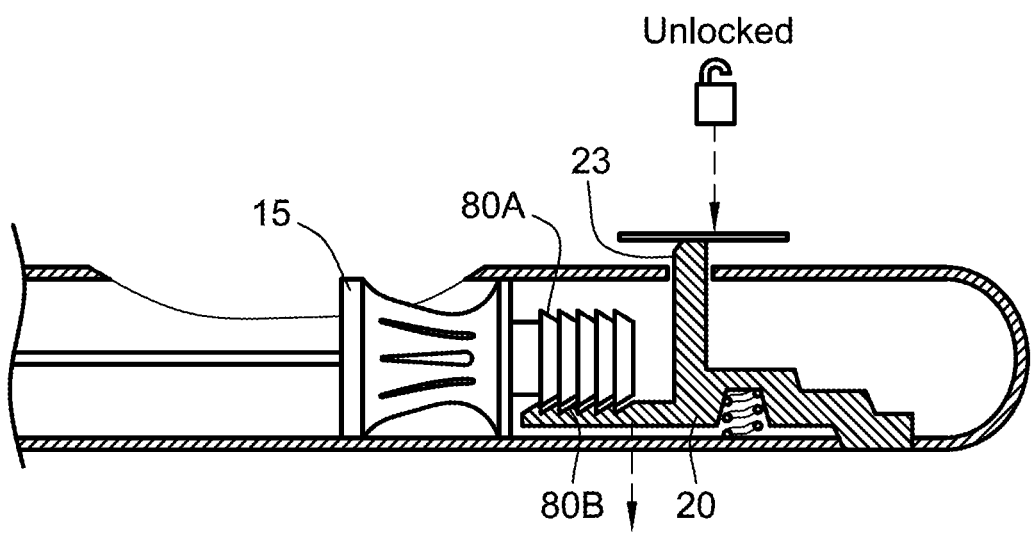
FIG. 12E is a cross-sectional view of a multipurpose handle incorporating an actuation button and locking member with a variable locking position.

In FIG. 12E, the multipurpose handle 1 may include the capability of providing variable locking positions during the operation of the delivery system. Variable locking positions may be created, without limitation, through the use of a plurality of splines, ridges, or teeth 80A located in the surface of the actuation button 15 that are appropriately mated or meshed with a plurality of grooves 80B formed in the locking member 20 or vice versa. The alignment or meshing of the splines 80A and the grooves 80B creates a locked position that prevents movement of the actuation button 15. The different number of splines 80A and grooves 80B that may be meshed or mated together establish variability in the position of the actuation button 15. The locking member 20 may include a locking button 23 in which pushing upon the locking button 23 causes the splines 80A and grooves 80B to separate, thereby, creating an unlocked position allowing the actuation button 15 to move.

Figure 13A:
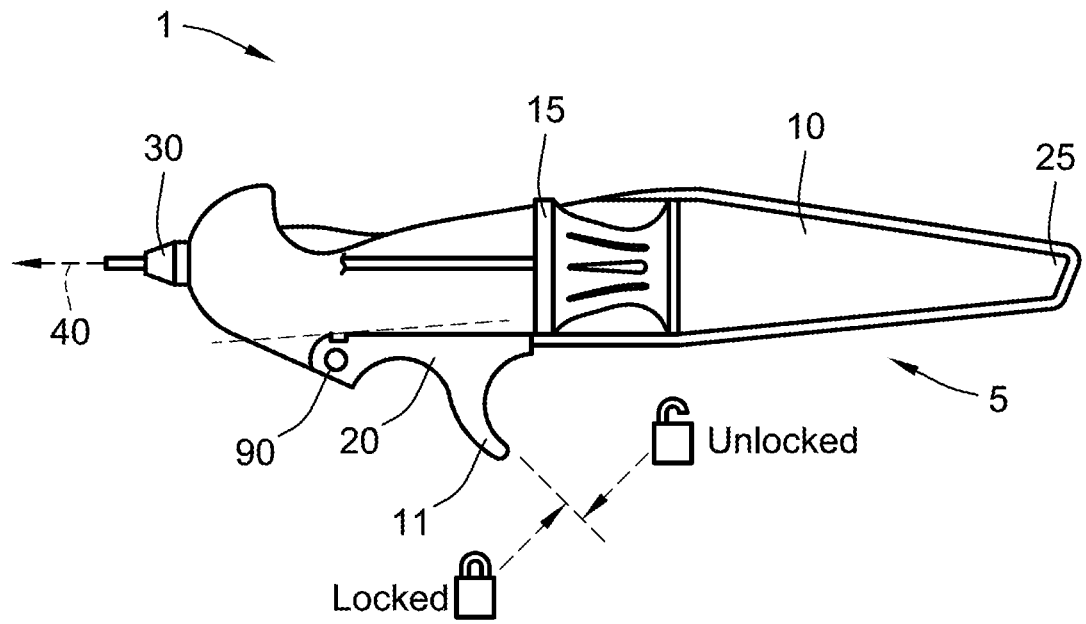
FIG. 13A and FIG. 13B are perspective views of medical device delivery systems that incorporate a multipurpose handle according to the teachings of the present disclosure.
Figure 13B:
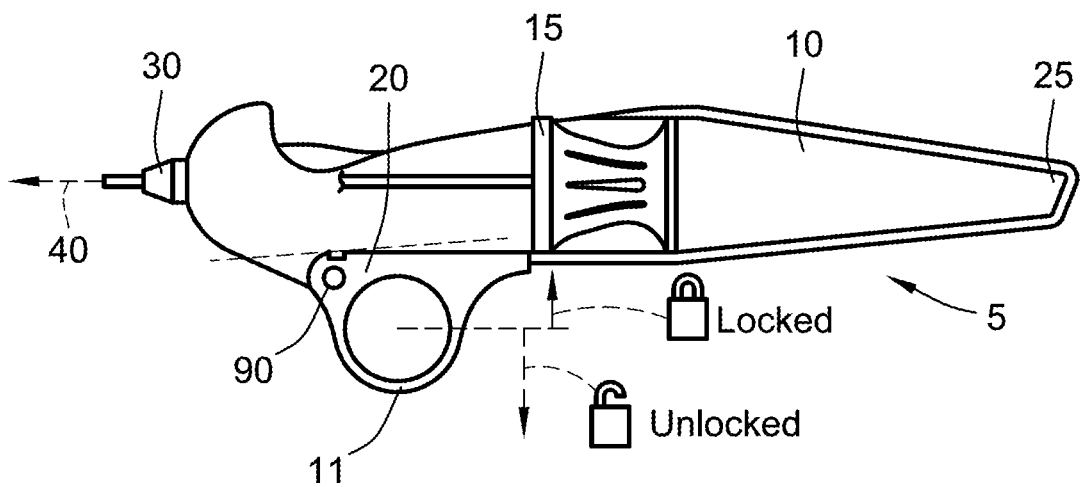

Referring now to FIGS. 13A and 13B, the locking member 20 may be integrated with the fin 11 formed as part of the elongate handle body 10. In this embodiment, the locking member 20 includes a pivot point 90 that allows the index finger of the user to apply pressure and push the locking member 20 into contact with the surface of a face 15A of the actuation button 15. The locking member 20 acts similar to a lever that is typically in an unlocked position and upon the application of external force or pressure by the user is forced into a locked position.

Figure 14:
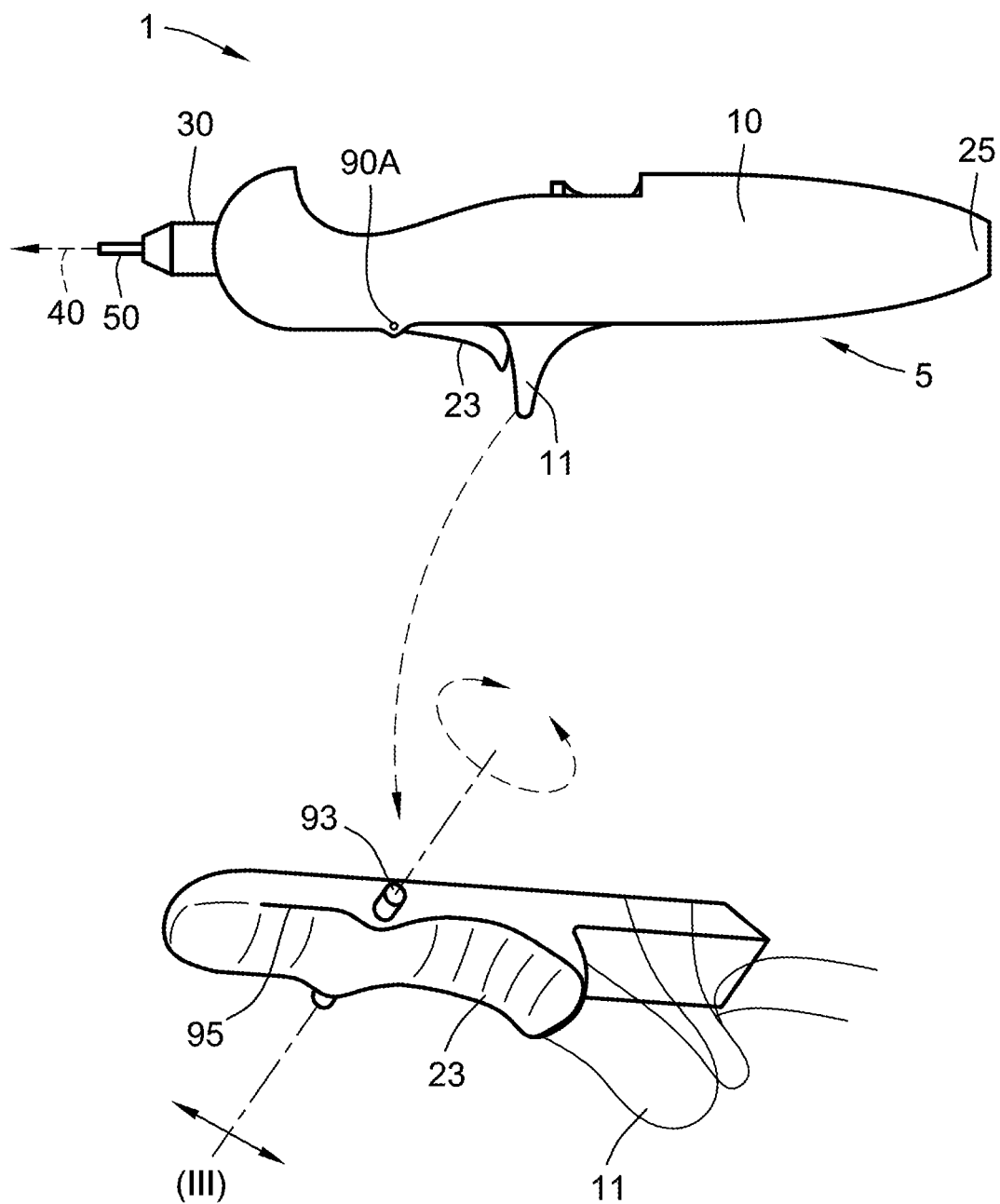
FIG. 14 is a perspective view of a medical device delivery system that incorporates a multipurpose handle with an expanded view of a locking button.

Another example of a medical device delivery system that incorporates the multipurpose handle of the present disclosure is described in FIG. 14. In this configuration the locking button 23 comprises at least one protrusion 93 located on each side of the locking button 23 in order to hold the button 23 in place and prevent the button 23 from being removed (i.e., falling) through the opening present in the elongated handle body 10. These protrusions 93 may also act as the pivot point 90A with respect to axis (III) in order for the locking button to establish a locked position and unlocked position. When desirable, the locking button 23 may also be ergonomically curved 95 so that it more appropriately fits the index finger of the user.

Figure 15:
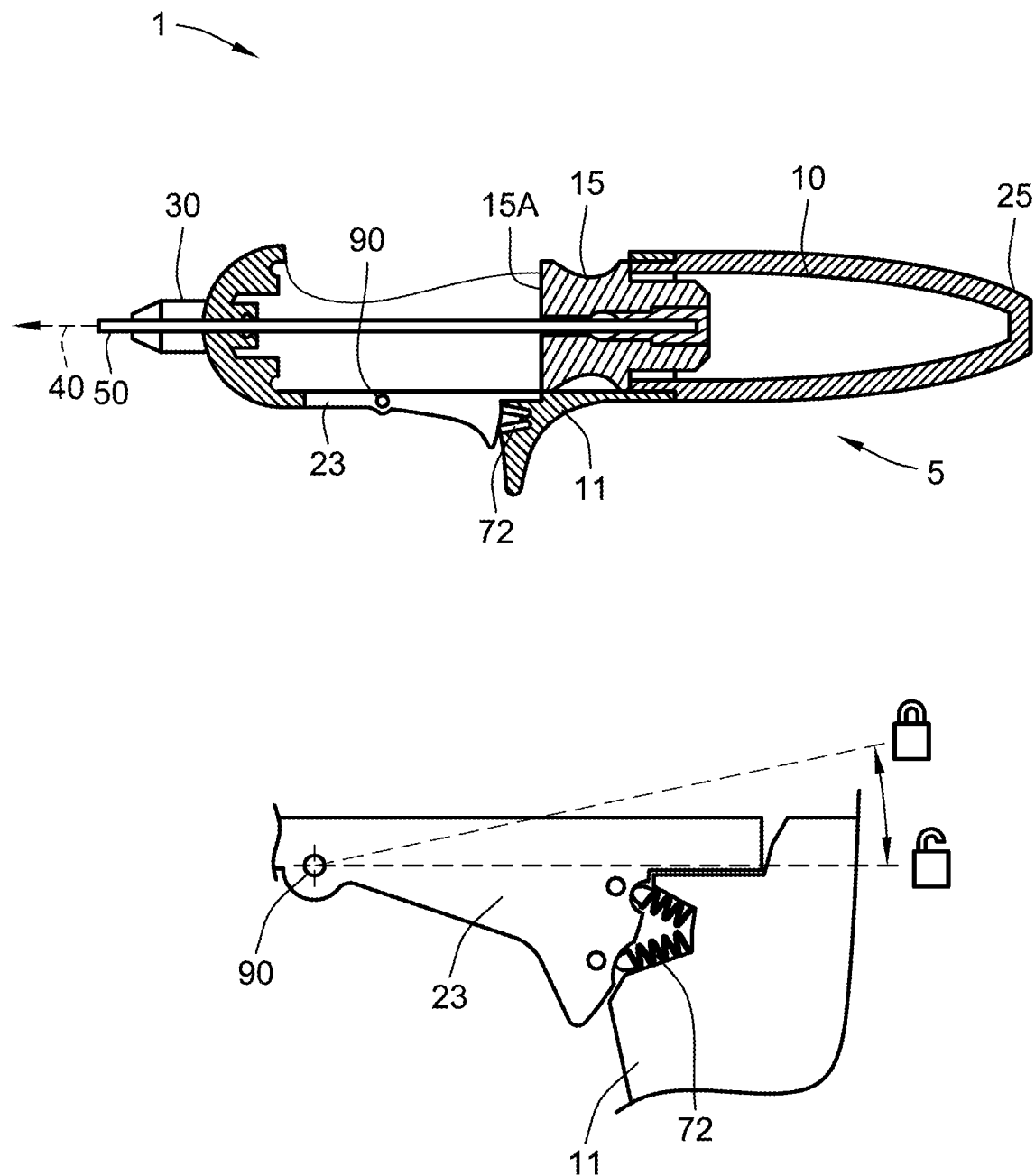
FIG. 15 is a cross-sectional view of a medical device delivery system incorporating a multipurpose handle with an expanded view of another locking button.

According to one aspect of the present disclosure, a locking button 23 is forced to abut against a face 15A of the actuation button, thereby, creating a locked position. The locking button 23 may be spring-loaded in that a spring forces the multipurpose handle to be in an unlocked or locked state in the absence of pressure applied by the user to the locking button 23. According to another aspect, the spring 72 as shown in FIG. 15, may provide a sensible and/or audible click associated with locking/unlocking the button 23. In the absence of pressure, the button 23 remains in the state in which it was left with subsequent locking or unlocking having to be done manually. In other words, an external force applied to the locking member that overcomes the force of the spring is able to cause the locking member to move from the unlocked position to the locked position or from the locked position to the unlocked position.

According to another aspect of the present disclosure, a medical device delivery system is provided that incorporates the multipurpose handle described above and as further defined herein. As shown in FIGS. 1-15, the medical device delivery system comprises an outer sheath, a medical device, and a multipurpose handle. The medical device is located at least partially within, alternatively, entirely within the outer sheath in an initial configuration ready for deployment. The outer sheath may be a catheter capable of holding and protecting the medical device while it is pushed endoluminally through a patient's vasculature to a remote treatment or targeted site. The outer sheath or catheter is advantageously as small in diameter as possible for a given application, in order to improve endovascular movement and hold the medical device properly in position until its deployment. The outer sheath may accommodate the use of a guide wire for tracking the delivery of the medical device to the desired or targeted position. The type of medical device is not restricted and may take the form of any known devices, including but not limited to, stents, embolic coils, and vena cava filters.

According to another aspect of the present disclosure, the use of a medical device delivery system that incorporates a multipurpose handle as described herein to deliver or retrieve a medical device from a desired or targeted site within a vasculature of a patient's body is believed to be within the scope of the present invention. During such use, the multipurpose handle provides the user with control over longitudinal movement together with scrolling rotation of the attached medical device. The user may utilize his/her thumb and index finger on a single hand to accomplish such longitudinal and rotational movements.

The specific examples provided in this disclosure are given to illustrate various embodiments of the invention and should not be construed to limit the scope of the disclosure. The embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Those skilled-in-the-art, in light of the present disclosure, will appreciate that many changes can be made in the specific embodiments which are disclosed herein and still obtain alike or similar result without departing from or exceeding the spirit or scope of the disclosure. One skilled in the art will further understand that any properties reported herein represent properties that are routinely measured and can be obtained by multiple different methods. The methods described herein represent one such method and other methods may be utilized without exceeding the scope of the present disclosure.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A multipurpose handle for delivery or retrieval of a medical device, the multipurpose handle comprising:
    an elongate handle body having a proximal end extending to a distal end defining a longitudinal axis, the elongate handle body having a cutout defining a movement space therein, the cutout including a longitudinal slot on an upper side of the elongate handle body opening to a cavity in the elongate handle body;
    a thumb wheel having a proximal face and a distal face, the thumb wheel disposed within the cutout of the elongate handle body with a portion received in the cavity and a portion exposed at the longitudinal slot for operation by a thumb of a hand of a user in a grip position gripping the elongate handle body, the thumb wheel connected to the medical device, the thumb wheel being movable within the cutout along the longitudinal axis and rotatable within the cutout;
    a locking member connected to the elongate handle body and movable between a locked position and an unlocked position, the locking member being positioned on a lower side of the elongate handle body opposite the upper side and accessible to and operable by an index finger of the hand of the user in the grip position, wherein upwardly pivoting movement of the locking member from the unlocked position to the locked position moves the locking member into the cavity and into direct abutting contact with the distal face of the thumb wheel and restricts movement of the thumb wheel along the longitudinal axis; and
    wherein the thumb wheel is connected to the medical device such that longitudinal movement of the thumb wheel within the cutout along the longitudinal axis moves the medical device longitudinally and rotation of the thumb wheel within the cutout rotates the medical device.

2. The multipurpose handle of claim 1, wherein the locking member is configured to have an unlocked state in which the locking member remains in the unlocked position until forced by a user to the locked position, and wherein the thumb wheel is movable slidably within the cutout along the longitudinal axis while the locking member remains in the unlocked state.

3. The multipurpose handle of claim 1, wherein the thumb wheel includes fins disposed on the circumference of the thumb wheel.

4. The multipurpose handle of claim 1, wherein the thumb wheel includes a tactile bump.

5. The multipurpose handle of claim 1, wherein the cutout is droplet shaped.

6. The multipurpose handle of claim 1, wherein the longitudinal axis of the elongate handle body and a longitudinal axis of the locking member are located such that the locking member rotates into the elongate handle body.

7. The multipurpose handle of claim 1, wherein the locking member includes a spring configured to hold the locking member in the locked position or unlocked position.

8. The multipurpose handle of claim 7, wherein the spring exhibits a force to hold the locking member in the locked position or the unlocked position, such that an external force applied to the locking member that overcomes the force of the spring is able to cause the locking member to move from the unlocked position to the locked position or from the locked position to the unlocked position.

9. The multipurpose handle of claim 1, wherein the thumb wheel further comprises one or more protrusions configured to prevent the thumb wheel from being removed from the elongate handle body.

10. A medical device delivery system comprising:
    an outer sheath;
    a medical device located at least partially within the outer sheath in an initial configuration ready for deployment; and
    a multipurpose handle connected to the outer sheath and the medical device, the handle comprising:

an elongate handle body having a proximal end extending to a distal end defining a longitudinal axis, the elongate handle body having a cutout defining a movement space therein, the cutout including a longitudinal slot on the elongate handle body opening to a cavity in the elongate handle body;

a thumb wheel disposed within the cutout of the elongate handle body with a portion received in the cavity and a portion exposed at the longitudinal slot for operation by a thumb of a hand of a user in a grip position gripping the elongate handle body, the thumb wheel connected to the medical device, the thumb wheel being movable slidably within the cutout along the longitudinal axis to move the medical device longitudinally and rotatable within the cutout to rotate the medical device;

a locking member connected to the elongate handle body and movable between a locked position and an unlocked position, the locking member being accessible to and operable by an index finger of the hand of the user in the grip position, wherein upwardly pivoting movement of the locking member from the unlocked position to the locked position moves the locking member into the cavity and into direct abutting contact with a distal face of the thumb wheel and restricts movement of the thumb wheel along the longitudinal axis.

11. The medical device delivery system of claim 10, wherein the medical device is a stent, an embolic coil, or a vena cava filter.

12. The medical device delivery system of claim 10, wherein the locking member is configured to have an unlocked state in which the locking member remains in the unlocked position until forced by a user to the locked position, and wherein the thumb wheel is movable slidably within the cutout along the longitudinal axis while the locking member remains in the unlocked state.

13. The medical device delivery system of claim 10, configured for delivering or retrieving the medical device from a targeted site in a vasculature of a patient.

14. A multipurpose handle for delivery or retrieval of a medical device, the multipurpose handle comprising:

an elongate handle body having a proximal end extending to a distal end defining a longitudinal axis, the elongate handle body having a cutout defining a movement space therein;

a thumb wheel having a proximal face and a distal face, the thumb wheel disposed within the cutout of the elongate handle body and connected to the medical device, the thumb wheel being movable within the cutout along the longitudinal axis and rotatable within the cutout;

a locking member connected to the elongate handle body and movable between a locked position and unlocked position, the locking member being in contact with the thumb wheel and restricting movement of the thumb wheel along the longitudinal axis in the locked position; and wherein the cutout is droplet shaped.

15. The multipurpose handle of claim 14, wherein in the locking position, the locking member is in contact with the distal face of the thumb wheel.

16. The multipurpose handle of claim 14, wherein the locking member includes a locking ring.

17. The multipurpose handle of claim 14, wherein the locking member includes a locking button configured to slide or be pushed in order to provide the locked position.

* * * * *